US011896417B2

(12) United States Patent
Wang

(10) Patent No.: US 11,896,417 B2
(45) Date of Patent: Feb. 13, 2024

(54) TIME-VARYING KINETIC MODELING OF HIGH TEMPORAL-RESOLUTION DYNAMIC PET DATA FOR MULTIPARAMETRIC IMAGING

(71) Applicant: The Regents of the University of California, Oakland, CA (US)

(72) Inventor: Guobao Wang, Sacramento, CA (US)

(73) Assignee: The Regents of the University of California, Oakland, CA (US)

( * ) Notice: Subject to any disclaimer, the term of this patent is extended or adjusted under 35 U.S.C. 154(b) by 840 days.

(21) Appl. No.: 16/959,829

(22) PCT Filed: Jan. 8, 2019

(86) PCT No.: PCT/US2019/012757
§ 371 (c)(1),
(2) Date: Jul. 2, 2020

(87) PCT Pub. No.: WO2019/136469
PCT Pub. Date: Jul. 11, 2019

(65) Prior Publication Data
US 2020/0367846 A1    Nov. 26, 2020

Related U.S. Application Data

(60) Provisional application No. 62/614,986, filed on Jan. 8, 2018.

(51) Int. Cl.
*A61B 6/00* (2006.01)
*G16H 50/50* (2018.01)
(Continued)

(52) U.S. Cl.
CPC ............ *A61B 6/5217* (2013.01); *A61B 6/037* (2013.01); *A61B 6/507* (2013.01); *A61K 51/04* (2013.01);
(Continued)

(58) Field of Classification Search
CPC ....... A61B 6/5217; A61B 6/037; A61B 6/507; G16H 50/50; G16H 30/40; A61K 51/04;
(Continued)

(56) References Cited

U.S. PATENT DOCUMENTS

2006/0173301 A1  8/2006 Darlas
2007/0112264 A1  5/2007 Wu et al.
(Continued)

FOREIGN PATENT DOCUMENTS

DE   102007039454 A1 * 2/2009 ........... G01R 33/481
WO   2014/012182 A1    1/2014

OTHER PUBLICATIONS

International Search Report and Written Opinion in PCT/US2019/012757 dated Apr. 15, 2019; 9 pages.
(Continued)

*Primary Examiner* — Khai M Nguyen
(74) *Attorney, Agent, or Firm* — Kilpatrick Townsend and Stockton LLP

(57) ABSTRACT

Systems and methods are disclosed for quantifying blood flow using time-varying kinetic modeling of high temporal-resolution dynamic positron emission tomography (PET) data. A single tracer is introduced into the body. A first set of images is acquired, via PET, of at least a portion of the body at a plurality of predetermined time intervals. Based on the first set of images, an intensity of the tracer in the at least the portion of the body is determined as a function of time. The intensity of the tracer as a function of time is modeled using a time-varying kinetic model. Based on the model, the blood flow through the at least the portion of the body is quantified. Additional images may be acquired and used to quantify additional parameter(s), such as glucose metabolism, amyloid load, etc., with the single tracer.

16 Claims, 9 Drawing Sheets

(51) Int. Cl.
*G16H 30/40* (2018.01)
*A61B 6/03* (2006.01)
*A61K 51/04* (2006.01)

(52) U.S. Cl.
CPC ...... *A61K 51/0455* (2013.01); *A61K 51/0482* (2013.01); *A61K 51/0491* (2013.01); *G16H 30/40* (2018.01); *G16H 50/50* (2018.01)

(58) Field of Classification Search
CPC ............ A61K 51/0455; A61K 51/0482; A61K 51/0491
See application file for complete search history.

(56) References Cited

U.S. PATENT DOCUMENTS

| | | | | |
|---|---|---|---|---|
| 2010/0008856 | A1* | 1/2010 | Wright | G01N 33/60 424/1.73 |
| 2010/0055036 | A1* | 3/2010 | Suhara | A61P 25/28 424/1.65 |
| 2013/0109964 | A1* | 5/2013 | Kelly | A61M 5/007 600/431 |
| 2015/0230762 | A1* | 8/2015 | Alpert | A61B 6/503 600/425 |
| 2017/0276809 | A1 | 9/2017 | Smith et al. | |
| 2018/0025512 | A1* | 1/2018 | Zhu | G06T 7/11 382/131 |

OTHER PUBLICATIONS

Abraham et al., 18F-FDG PET Imaging of Myocardial Viability in an Experienced Center with Access to 18F-FDG and Integration with Clinical Management Teams: the Ottawa-Five Substudy of the PARR 2 Trial, Journal of Nuclear Medicine, vol. 51, No. 4, Apr. 2010, pp. 567-574.
Afonso et al., Fast Image Recovery Using Variable Splitting and Constrained Optimization, IEEE Transactions on Image Processing, vol. 19, No. 9, 2010, pp. 2345-2356.
Allman, Noninvasive Assessment Myocardial Viability: Current Status and Future Directions, Journal of Nuclear Cardiology, 2013. vol. 20, No. 4, 2013, pp. 618-637.
Antsaklis et al., Linear Systems, New York: McGraw-Hill, 1997.
Baikejiang et al., Anatomical Image-guided Fluorescence Molecular Tomography Reconstruction Using Kernel Method, Journal of Biomedical Optics, vol. 22, No. 5, May 1, 2017, 14 pages.
Baikejiang et al., Kernel-based Anatomically-aided Diffuse Optical Tomography Reconstruction, Biomedical Physics & Engineering Express, vol. 3, No. 5, Sep. 13, 2017, 18 pages.
Berman et al., Phase II Safety and Clinical Comparison with Single-Photon Emission Computed Tomography Myocardial Perfusion Imaging for Detection of Coronary Artery Disease Flurpiridaz F 18 Positron Emission Tomography, Journal of the American College of Cardiology, vol. 61, No. 4, Jan. 29, 2013, pp. 469-477.
Bernstine et al., FDG PET/CT Early Dynamic Blood Flow and Late Standardized Uptake Value Determination in Hepatocellular Carcinoma, Radiology, vol. 260, No. 2, Aug. 2011, pp. 503-510.
Bisdas et al., Whole-Tumor Perfusion CT Parameters and Glucose Metabolism Measurements in Head and Neck Squamous Cell Carcinomas: A Pilot Study Using Combined Positron-Emission Tomography/CT Imaging, American Journal of Neuroradiology, vol. 29, No. 7, Aug. 2008, pp. 1376-1381.
Black et al., Rapid Multi-Tracer Pet Tumor Imaging With F-18-fdg and Secondary Shorter-lived Tracers, Institute of Electrical and Electronics Engineers Transactions on Nuclear Science, vol. 56, No. 5, Oct. 2009, pp. 2750-2758.
Bland et al., Statistical Methods for Assessing Agreement Between Two Methods of Clinical Measurement, The Lancet, vol. 327, No. 8476, Feb. 8, 1986, pp. 307-310.
Boellaard et al., FDG PET/CT: Eanm Procedure Guidelines for Tumour Imaging: Version 2.0, European Journal of Nuclear Medicine and Molecular Imaging, vol. 42, No. 2, 2015, pp. 328-354.
Buck et al., Economic Evaluation of PET and PET/CT in Oncology: Evidence and Methodologic Approaches, Journal of Nuclear Medicine Technology, vol. 51, No. 3, Mar. 2010, pp. 401-412.
Calamante et al., Bolus Delay and Dispersion in Perfusion MRI: Implications for Tissue Predictor Models in Stroke, Magnetic Resonance in Medicine, vol. 55, No. 5, May 2006, pp. 1180-1185.
Camici et al., Stunning, Hibernation, and Assessment of Myocardial Viability, Circulation, vol. 117, No. 1, Jan. 1-8, 2008, pp. 103-114.
Carson, Tracer Kinetic Modeling in PET, in Positron Emission Tomography, 2005, 33 pages.
Cheong et al., Dynamic Contrast-Enhanced CT of Intracranial Meningioma: Comparison of Distributed and Compartmental Tracer Kinetic Models—Initial Results, Radiology, vol. 232, No. 3, Sep. 2004, pp. 921-930.
Cherry et al., Total-Body Imaging: Transforming the Role of Positron Emission Tomography, Science Translational Medicine, vol. 9, No. 381, Mar. 2017, 7 pages.
Cherry et al., Total-Body PET: Maximizing Sensitivity to Create New Opportunities for Clinical Research and Patient Care, The Journal of Nuclear Medicine, vol. 59, No. 1, Jan. 2018, pp. 3-12.
Cochet et al., Evaluation of Breast Tumor Blood Flow with Dynamic First-Pass F 18-FDG PET/CT: Comparison with Angiogenesis Markers and Prognostic Factors, Journal of Nuclear Medicine, 2012, vol. 53, No. 4, Apr. 2012, pp. 512-520.
Davenport et al., Contrast Material-induced Nephrotoxicity and Intravenous Low-Osmolality Iodinated Contrast Material: Risk Stratification by Using Estimated Glomerular Filtration Rate, Radiology, 2013, vol. 268, No. 3, Sep. 2013, pp. 719-728.
Di Carli et al., Clinical Myocardial Perfusion PET/CT, Journal of Nuclear Medicine, vol. 48, No. 5, May 2007, pp. 783-793.
Doraiswamy et al., Amyloid-Beta Assessed by Florbetapir F 18 Pet and 18-Month Cognitive Decline a Multicenter Study, Neurology, vol. 79, No. 16, 2012.
El Fakhri et al., Quantitative Dynamic Cardiac Rb-82 PET Using Generalized Factor and Compartment Analyses, Journal of Nuclear Medicine, vol. 46, No. 8, Aug. 2005, pp. 1264-1271.
Essig et al., Perfusion MRI: The Five Most Frequently Asked Clinical Questions, American Journal of Roentgenology, vol. 200, No. 1, Jan. 2013, 22 pages.
El Fakhri et al., Reproducibility and Accuracy of Quantitative Myocardial Blood Flow Assessment with 82Rb PET: Comparison with 13N-Ammonia PET, The Journal of Nuclear Medicine, vol. 50, No. 7, 2009, pp. 1062-1071.
Fessler, Mean and Variance of Implicitly Defined Biased Estimators (Such as Penalized Maximum Likelihood): Applications to Tomography, IEEE Transactions on Image Processing, vol. 5, No. 3, Mar. 1996, 16 pages.
Fessler et al., Spatial Resolution Properties of Penalized-likelihood Image Reconstruction: Space-invariant Tomographs, IEEE Transactions on Image Processing, vol. 5, No. 9, 1996, pp. 1346-1358.
Fischer et al., Integrated F-18-FDG PET/Perfusion CT for the Monitoring of Neoadjuvant Chemoradiotherapy in Rectal Carcinoma: Correlation with Histopathology, European Journal of Nuclear Medicine and Molecular Imaging, vol. 41, No. 8, Aug. 2014, pp. 1563-1573.
Gaddikeri et al., Dynamic Contrast-Enhanced MR Imaging in Head and Neck Cancer: Techniques and Clinical Applications, American Journal of Neuroradiology, vol. 37, Apr. 2016, pp. 588-595.
Goh et al., Radiation Dose from Volumetric Helical Perfusion CT of the Thorax, Abdomen or Pelvis, European Radiology, vol. 21, No. 5, May 2011, pp. 974-981.
Goh et al., The Flow-Metabolic Phenotype of Primary Colorectal Cancer: Assessment by Integrated F-18-FDG PET/Perfusion CT with Histopathologic Correlation, Journal of Nuclear Medicine, vol. 53, No. 5, May 2012, pp. 687-692.
Gong et al., Direct Patlak Reconstruction from Dynamic PET Data Using the Kernel Method with MRI Information Based on Structural Similarity, IEEE Transactions on Medical Imaging, vol. 37, No. 4, Apr. 2018, pp. 955-965.

(56) References Cited

OTHER PUBLICATIONS

Gronroos et al., Hypoxia, Blood Flow and Metabolism in Squamous-Cell Carcinoma of the Head and Neck: Correlations Between Multiple Immunohistochemical Parameters and PET, BMC Cancer, vol. 14, Nov. 24, 2014, pp. 1-11.

Guo et al., F-18-alfatide li and F-18-fdg Dual-tracer Dynamic Pet for Parametric, Early Prediction of Tumor Response to Therapy, Journal of Nuclear Medicine, vol. 55, No. 1, Jan. 2014, pp. 154-160.

Hanahan et al., Hallmarks of Cancer: The Next Generation, Cell, vol. 144, No. 5, Mar. 4, 2011, pp. 646-674.

Ho et al., Dual-tracer Pet/ct Imaging in Evaluation of Metastatic Hepatocellular Carcinoma, Journal of Nuclear Medicine, vol. 48, No. 6, Jun. 2007, pp. 902-909.

Hoang et al., Estimation of Radiation Exposure for Brain Perfusion CT: Standard Protocol Compared with Deviations in Protocol, American Journal of Roentgenology, vol. 201, No. 5, Nov. 2013, pp. W730-W734.

Hosteter et al., Effects of Pair Bonding Increases Dopamine D1 Receptors in Monogamous Male Titi Monkeys (*Callicebus cupreus*), American Journal of Primatology, vol. 79, No. 3, Mar. 2017, 19 pages.

Humbert et al., Breast Cancer Blood Flow and Metabolism on Dual-acquisition F-18-FDG Pet:Correlation With Tumor Phenotype and Neoadjuvant Chemotherapy Response, Journal of Nuclear Medicine, vol. 59, No. 7, Feb. 9, 2018, pp. 1035-1041.

Hutchcroft et al., Anatomically-aided PET Reconstruction Using the Kernel Method, Physics in medicine and biology, vol. 61, No. 18, Sep. 21, 2016, pp. 6668-6683.

Ibaraki et al., Tracer Delay Correction of Cerebral Blood Flow with Dynamic Susceptibility Contrast-Enhanced MRI, Journal of Cerebral Blood Flow and Metabolism, vol. 25, No. 3, 2005, pp. 378-390.

Jansen et al., Tumor Metabolism and Perfusion in Head and Neck Squamous Cell Carcinoma: Pretreatment Multimodality Imaging with 1H-Magnetic Resonance Spectroscopy, Dynamic Contrast-Enhanced MRI and 18F-FDG PET, Journal of Radiation Oncology Biology Physics, vol. 82, No. 1, Jan. 1, 2012, pp. 299-307.

Kadrmas et al., Feasibility of Rapid Multitracer Pet Tumor Imaging, Institute of Electrical and Electronics Engineers Transactions on Nuclear Science, vol. 52, No. 5, Oct. 2005, pp. 1341-1347.

Kershaw et al., Temporal Resolution and SNR Requirements for Accurate DCE-MRI Data Analysis Using the AATH Model, Magnetic Resonance in Medicine, vol. 64, No. 6, Dec. 2010, pp. 1772-1780.

Kim et al., Combining Ordered Subsets and Momentum for Accelerated X-Ray CT Image Reconstruction, Institute of Electrical and Electronics Engineers Transactions on Medical Imaging, vol. 34, No. 1, Jan. 2015, pp. 167-178.

Kim et al., Voxelwise Lp-ntPET for Detecting Localized, Transient Dopamine Release of Unknown Timing: Sensitivity Analysis and Application to Cigarette Smoking in the Pet Scanner, Human Brain Mapping, vol. 35, No. 9, Apr. 3, 2014, pp. 4876-4891.

Komar et al., Decreased Blood Flow with Increased Metabolic Activity: A Novel Sign of Pancreatic Tumor Aggressiveness, Clinical Cancer Research, vol. 15, No. 7, Sep. 1, 2009, pp. 5511-5517.

Kudo et al., Difference in Tracer Delay-Induced Effect Among Deconvolution Algorithms in CT Perfusion Analysis: Quantitative Evaluation with Digital Phantoms, Radiology, vol. 251, No. 1, Apr. 2009, pp. 241-249.

St. Lawrence et al., An Adiabatic Approximation to the Tissue Homogeneity Model for Water Exchange in the Brain: I. Theoretical Derivation, Journal of Cerebral Blood Flow and Metabolism, vol. 18, No. 12, 1998, pp. 1365-1377.

Lohrke et al., 25 Years of Contrast-Enhanced MRI: Developments, Current Challenges and Future Perspectives, Advances in Therapy, vol. 33, 2016, pp. 1-28.

Maddahi, Properties of an Ideal PET Perfusion Tracer: New PET Tracer Cases and Data, Journal of Nuclear Cardiology, vol. 19, Jan. 19, 2012, pp. S30-S37.

Mankoff et al., Blood Flow-Metabolism Mismatch: Good for the Tumor, Bad for the Patient, Clinical Cancer Research, vol. 15, No. 17, Sep. 1, 2009, pp. 5294-5296.

Mehanna et al., PET-CT Surveillance Versus Neck Dissection in Advanced Head and Neck Cancer, New England Journal of Medicine, 2016, pp. 1444-1454.

Mullani et al., Tumor Blood Flow Measured by PET Dynamic Imaging of First-Pass F-18-FDG Uptake: A Comparison with 0-15-Labeled Water-Measured Blood Flow, Journal of Nuclear Medicine, vol. 49, No. 4, Apr. 2008, pp. 517-523.

Muzic et al., Distributed Versus Compartment Models for PET Receptor Studies, Institute of Electrical and Electronics Engineers Transactions on Medical Imaging, vol. 22, No. 1, Jan. 2003, pp. 11-21.

Normandin et al., Estimating Neurotransmitter Kinetics With ntPET: A Simulation Study of Temporal Precision and Effects of Biased Data, Neuroimage, vol. 39, No. 3, 2008, pp. 1162-1179.

Novosad et al., MR-guided Dynamic Pet Reconstruction with the Kernel Method and Spectral Temporal Basis Functions, Physics in Medicine and Biology, vol. 61, No. 12, May 26, 2016, pp. 4624-4645.

Ostergaard et al., Capillary Transit Time Heterogeneity and Flow-Metabolism Coupling After Traumatic Brain Injury, Journal of Cerebral Blood Flow and Metabolism, vol. 34, No. 10, Oct. 2014, pp. 1585-1598.

Parent, E.E. and D.M. Schuster, *Update on F-18-Fluciclovine PET for Prostate Cancer Imaging.* Journal of Nuclear Medicine, 2018. 59(5): p. 733-739.

Qi et al., A Theoretical Study of the Contrast Recovery and Variance of MAP Reconstructions from PET Data, IEEE Transactions on Medical Imaging, vol. 18, No. 4, Apr. 1999, pp. 293-305.

Qi et al., A Unified Noise Analysis for Iterative Image Estimation, Physics in Medicine and Biology, vol. 48, No. 21, Oct. 10, 2003, 17 pages.

Qi et al., Iterative Reconstruction Techniques in Emission Computed Tomography, Physics in Medicine and Biology, vol. 51, No. 15, Aug. 7, 2006, pp. R541-R578.

Qi et al., Resolution and Noise Properties of MAP Reconstruction for Fully 3-D PET, IEEE Transactions on Medical Imaging, vol. 19, No. 5, May 2000, pp. 493-506.

Rahmim et al., Four-dimensional (4D) Image Reconstruction Strategies in Dynamic Pet: Beyond Conventional Independent Frame Reconstruction, Medical Physics, vol. 36, No. 8, Aug. 2009, pp. 3654-3670.

Rajendran, Hypoxia and Glucose Metabolism in Malignant Tumors: Evaluation by F-18 Fluoromisonidazole and F-18 Fluorodeoxyglucose Positron Emission Tomography Imaging, Clinical Cancer Research, vol. 10, No. 7, Apr. 2004, pp. 2245-2252.

Reader et al., 4D Image Reconstruction for Emission Tomography, Physics in Medicine and Biology, vol. 59, No. 22, Oct. 31, 2014, pp. R371-R418.

Richard et al., Determination of an Optimal Pharmacokinetic Model of F-18-FET for Quantitative Applications in Rat Brain Tumors, Journal of Nuclear Medicine, vol. 58, No. 8, Aug. 2017, pp. 1278-1284.

Schmidt et al., Kinetic Modeling in Positron Emission Tomography, Quarterly Journal of Nuclear Medicine, 2002, vol. 46, No. 1, 2002, pp. 70-85.

Schoder et al., Head and Neck Cancer: Clinical Usefulness and Accuracy of PET/CT Image Fusion, Radiology, vol. 231, No. 1, 2004, pp. 65-72.

Shukla-Dave et al., Dynamic Contrast-Enhanced Magnetic Resonance Imaging as a Predictor of Outcome in Head-and-Neck Squamous Cell Carcinoma Patients with Nodal Metastases, International Journal of Radiation Oncology Biology Physics, vol. 82, No. 5, Apr. 2012, pp. 1837-1844.

Sourbron et al., Tracer Kinetic Modelling in MRI: Estimating Perfusion and Capillary Permeability, Physics in Medicine and Biology, vol. 57, No. 2, Jan. 21, 2012, pp. R1-R33.

Spencer et al., Dynamic PET Image Reconstruction for Parametric Imaging using the HYPR Kernel Method, in Medical Imaging 2017: Physics of Medical Imaging, SPIE Medical Imaging, Available Online at: https://www.spiedigitallibrary.org/conference-proceedings-

(56) References Cited

OTHER PUBLICATIONS of-spie/10132/101324W/Dynamic-PET-Image-reconstruction-for-parametric-imaging-using-the-HYPR/10.1117/12.2254497.short?SSO=1, 2017, 8 pages.
Srirajaskanthan et al., The Role of Ga-68-dotatate Pet in Patients with Neuroendocrine Tumors and Negative or Equivocal Findings on in-111-dtpa-octreotide Scintigraphy, Journal of Nuclear Medicine, vol. 51, No. 6, 2010, pp. 875-882.
Velazquez et al., Coronary-Artery Bypass Surgery in Patients with Ischemic Cardiomyopathy, The New England Journal of Medicine, vol. 374, No. 16, Apr. 21, 2016, pp. 1511-1520.
Venkat et al., New Insights into Coupling and Uncoupling of Cerebral Blood Flow and Metabolism in the Brain, Croatian Medical Journal, vol. 57, No. 3, Jun. 30, 2016, pp. 223-228.
Verfaillie et al., Cerebral Perfusion and Glucose Metabolism in Alzheimer's Disease and Frontotemporal Dementia: Two Sides of the Same Coin? European Radiology, vol. 25, No. 10, Apr. 2015, pp. 3050-3059.
Wang et al., A Framework for Designing Dynamic Lp-ntPET Studies to Maximize the Sensitivity to Transient Neurotransmitter Responses to Drugs: Application to Dopamine and Smoking, Neuroimage, vol. 146, Feb. 1, 2017, pp. 701-714.
Wang et al., Accelerated Direct Reconstruction of Pet Parametric Images Using Augmented Lagrangian Optimization, 2015 Institute of Electrical and Electronics Engineers 12th International Symposium on Biomedical Imaging, Apr. 16-19, 2015, pp. 1200-1203.
Wang et al., Acceleration of the Direct Reconstruction of Linear Parametric Images Using Nested Algorithms, Physics in Medicine and Biology, vol. 55, No. 5, Mar. 7, 2010, pp. 1505-1517.
Wang et al., An Optimization Transfer Algorithm for Nonlinear Parametric Image Reconstruction from Dynamic Pet Data, Institute of Electrical and Electronics Engineers Transactions on Medical Imaging, vol. 31, No. 10, Oct. 2012, pp. 1977-1988.
Wang et al., Analysis of Penalized Likelihood Image Reconstruction for Dynamic PET Quantification, IEEE Transactions on Medical Imaging, vol. 28, No. 4, Apr. 2009, pp. 608-620.
Wang et al., Direct Estimation of Kinetic Parametric Images for Dynamic PET, Theranostics, vol. 3, No. 10, 2013, pp. 802-815.
Wang et al., Dynamic PET of Human Liver Inflammation: Impact of Kinetic Modeling with Optimization-Derived Dual-Blood Input Function, Physics in Medicine and Biology, vol. 63, No. 15, Jul. 24, 2018, 29 pages.
Wang et al., Generalized Algorithms for Direct Reconstruction of Parametric Images from Dynamic Pet Data, Institute of Electrical and Electronics Engineers Transactions on Medical Imaging, vol. 28, No. 11, Nov. 2009, pp. 1717-1726.
Wang, High Temporal-Resolution Dynamic PET Image Reconstruction Using a New Spatiotemporal Kernel Method, IEEE Transactions on Medical Imaging, vol. 38, No. 3, Sep. 2018, pp. 1-11.
Wang, High Temporal-Resolution Dynamic PET Image Reconstruction Using a New Spatiotemporal Kernel Method, in 14th International Meeting on Fully Three-Dimensional Image Reconstruction in Radiology and Nuclear Medicine, Jun. 2017, pp. 1-5.
Wang et al., Maximum a Posteriori Reconstruction of the Patlak Parametric Image from Sinograms in Dynamic PET, Physics in Medicine and Biology, vol. 53, No. 3, Feb. 7, 2008, pp. 593-604.
Wang et al., Penalized Likelihood PET Image Reconstruction Using Patch-Based Edge-Preserving Regularization, Institute of Electrical and Electronics Engineers Transactions on Medical Imaging, vol. 31, Issue 12, Dec. 2012, pp. 2194-2204.
Wang et al., PET Image Reconstruction Using Kernel Method, Institute of Electrical and Electronics Engineers Transactions on Medical Imaging, vol. 34, No. 1, Jan. 2015, pp. 61-71.
Wang et al., Time-Varying Kinetic Modeling of High Temporal-Resolution Dynamic 18F-FDG PET Data for Multiparametric Imaging, Journal of Nuclear Medicine, vol. 59, 2018, pp. 503-503.
Winterdahl et al., Hepatic Blood Perfusion Measured by 3-Minute Dynamic F 18 FDG PET in Pigs, Journal of Nuclear Medicine, 2011, vol. 52, No. 7, Jul. 2011, pp. 1119-1124.
Wintermark et al., Dynamic Perfusion CT: Optimizing the Temporal Resolution and Contrast Volume for Calculation of Perfusion CT Parameters in Stroke Patients, American Journal of Neuroradiology, vol. 25, No. 5, May 2004, pp. 720-729.
Zierler, A Critique of Compartmental Analysis, Annual Review of Biophysics and Bioengineering, vol. 10, 1981, pp. 531-562.
Zuo et al., Relative Patlak Plot for Dynamic PET Parametric Imaging Without the Need for Early-Time Input Function, Physics in Medicine and Biology, vol. 63, No. 16, Aug. 10, 2018, 15 pages.

* cited by examiner

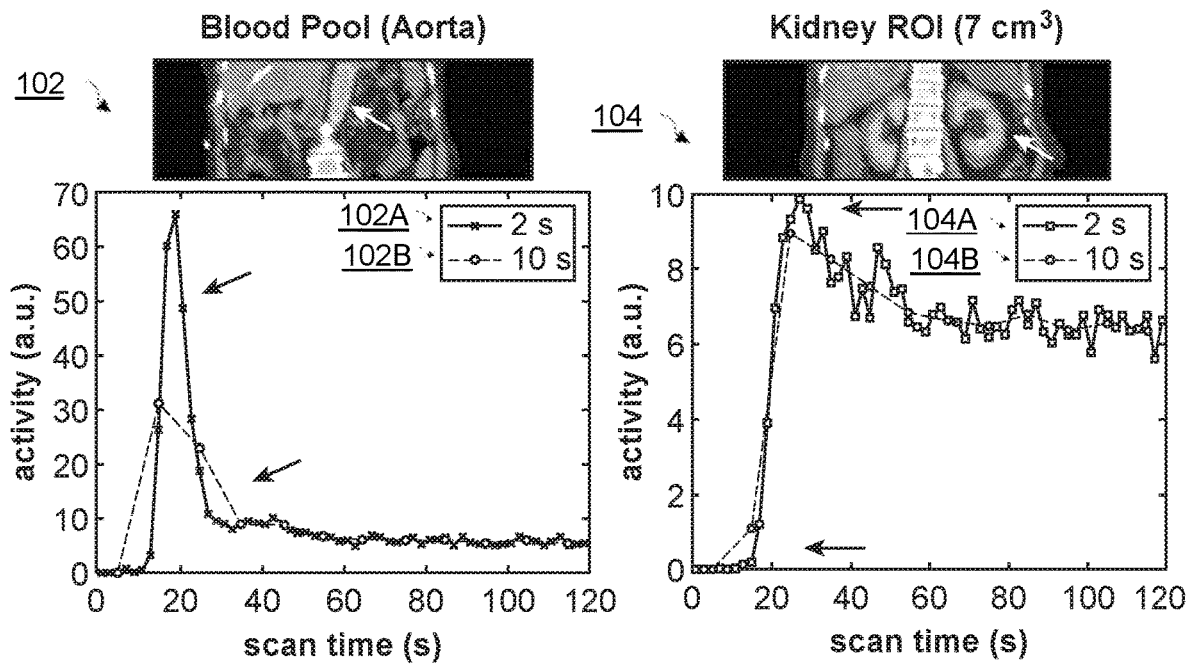
FIG. 1A
FIG. 1B
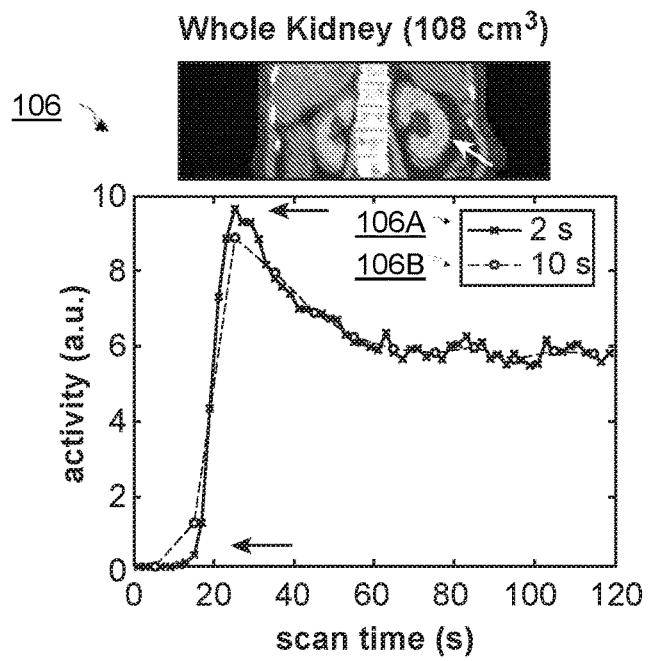
FIG. 1C

200

$$C_T(t) = (1-f_v)[C_1(t)+C_2(t)] + f_v C_{wb}(t)$$

TIME-VARYING KINETIC MODELING OF HIGH TEMPORAL-RESOLUTION DYNAMIC PET DATA FOR MULTIPARAMETRIC IMAGING

CROSS-REFERENCE TO RELATED APPLICATION

This application is a US National Phase Application Under Section 371 of PCT/US2019/012757, filed Jan. 8, 2019, which claims priority to U.S. Provisional Application No. 62/614,986, filed on Jan. 8, 2018, the contents of each of which are incorporated by reference herein in their entireties.

BACKGROUND

Positron emission tomography (PET) imaging is a method of imaging molecular processes in the body. In an effort to assess vital physiological processes in the living body, a radioactive tracer is administered to a subject. The radioactive tracer may be injected, or, in some cases, inhaled. The subject is placed into a PET scanner for image acquisition. The images are fit to a mathematical model, for determining a parameter indicative of a molecular process. Typically, a single parameter is measured using the PET images. For example, PET imaging is used to quantify parameters representing a vital physiological process such as glucose metabolism, amyloid load, and blood flow. Each parameter is typically measured using different radiotracers and methods than other parameters. For example, glucose metabolism is commonly measured with the radiotracer $^{18}$F-fluorodeoxyglucose (FDG). Blood flow is commonly measured with other radiotracers such as $^{15}$O-water, $^{13}$N-ammonia, or $^{82}$Rb-chloride.

PET images include multiple layers of data, from which the desired parameters must be extracted. The desired parameters are quantified through mathematical modeling. The mathematical models frequently use "compartments" to model the images. A compartment is characterized by a particular chemical species in a particular physical space. For example, FDG molecules may be measured in several compartments, such as FDG in blood, FDG in lung tissue, and/or the like. A model may be based on one or more compartments, and may be referred to as a one-compartment model, a two-compartment model, etc., based on the number of compartments included in the model.

Blood flow and glucose metabolism are two basic but vital physiological processes in the living body. The phenomenon of flow-metabolism mismatch or coupling is of broad clinical and research significance in many diseases. For example, in ischemic cardiomyopathy, which affects several million people in the United States, myocardial flow-metabolism mismatch is used for assessing tissue viability to select patients for surgical revascularization. Decreased myocardial blood flow to myocardial segments that maintain myocardial glucose metabolism indicates flow-metabolism mismatch and suggests the myocytes are still alive (while hibernating) and thus can benefit from revascularization. As another example, in cancer, altered blood flow and glucose metabolism are closely related to two hallmarks of cancer—angiogenesis and increased cell metabolism, which can double indicate cancer cells are aggressively growing and resistant to therapy. As another example, in the normal brain, cerebral blood flow and glucose metabolism are often coupled with each other but may become uncoupled in neurodegenerative diseases.

Thus, there are critical interests and wide needs for integrated imaging of perfusion and metabolism in both clinical and research applications. Multiple parameters are currently measured using multiple radiotracers. However, using such a two-tracer (e.g., $^{82}$Rb-chloride+FDG) method for flow-metabolism imaging is resource-intensive with long imaging time and significant cost.

BRIEF SUMMARY

Embodiments include methods as well as systems for quantifying blood flow using time-varying kinetic modeling of high temporal-resolution dynamic positron emission tomography (PET) data. Blood flow may be derived without the need for a flow-specific radiotracer, thus enabling multiparametric imaging using a single radiotracer.

One embodiment is directed to a method comprising: introducing a single tracer into the body; acquiring, via positron emission tomography (PET), a first set of images of at least a portion of the body, wherein the first set of images is acquired at a first plurality of predetermined time intervals; based on the first set of images, determining an intensity of the tracer in the at least the portion of the body as a function of time; modeling the intensity of the tracer in the at least the portion of the body as a function of time using a time-varying kinetic model; and, based on the model, quantifying the blood flow through the at least the portion of the body.

Another embodiment is directed to a system comprising a computer programmed to perform the above-noted method.

Another embodiment is directed to a computer-program product programmed to perform the above-noted method.

BRIEF DESCRIPTION OF THE DRAWINGS

FIGS. 1A-1C illustrate standard temporal resolution (10-s) and high temporal resolution (2-s) sampling for early-dynamic FDG-PET in three regions of interest according to various embodiments.

DETAILED DESCRIPTION

A. Definitions

Figure 2:
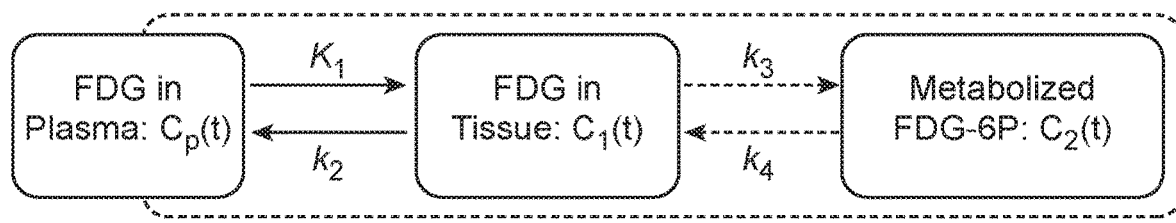
FIG. 2 illustrates a standard 3-compartment model for FDG kinetics according to various embodiments.

Prior to discussing some embodiments, some terms can be described in further detail.

The term "subject," as used herein, refers to any living organism that is suitable for being imaged by the methods described herein. Such organisms include, but are not limited to, human, dog, cat, horse, cow, sheep, goat, mouse, rat, guinea pig, monkey, avian, reptiles, bacteria, fungi, and the like.

A "tracer," or "radiotracer" is a chemical compound with one or more atoms replaced with a radioisotope. A tracer may be administered to a subject (e.g., by intravenous injection or inhalation) prior to imaging to highlight certain features. Imaging may then be conducted with methods such as Positron Emission Tomography (PET), Single Photon Emission Computed Tomography (SPECT), and/or the like. Examples of tracers include, but are not limited to, $^{18}$F-fluorodeoxyglucose (FDG), $^{15}$O-water, $^{13}$N-ammonia, $^{82}$Rb-chloride, $^{18}$F-fluciclovine, $^{18}$F-AV-45, and $^{68}$Ga-DOTATATE.

The term "tissue," as used herein, refers to a group of cells in a subject's body. Nonlimiting examples of tissues include tissues from organs such as brain, heart, lung, liver, stomach, pancreas, colon, rectum, intestines, blood vessels, arteries, and the like.

The term "extraction fraction," as used herein, refers to a percentage of a tracer moving from a first medium to a second medium. For example, the extraction fraction of a tracer moving from blood to tissue may be measured. The extraction fraction E may be determined as a function of the blood flow F and the product of tracer permeability (P) and surface area (S) in a tissue region. The extraction fraction varies based on both the type of tracer used and the tissue region of interest.

Unless specifically stated or obvious from context, as used herein, the term "about" is understood as within a range of normal tolerance in the art, for example within 2 standard deviations of the mean. "About" can be understood as within 10%, 9%, 8%, 7%, 6%. 5%, 4%, 3%, 2%, 1%, 0.5%, 0.1%, 0.05%, or 0.01% of the stated value. Unless otherwise clear from context, all numerical values provided herein are modified by the term about.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

B. Overview

Positron emission tomography (PET) may be used, subsequent to admission of a tracer to the body, to image at least a portion of the body where the tracer travels. Portions of the body to be imaged may include, as nonlimiting examples, a heart, a brain, a kidney, a lung, a liver, a spleen, a breast, a colon, or a prostate. PET is commonly used to image a region containing a tumor.

Clinical imaging of flow-metabolism mismatch or coupling is not trivial. The main barrier for perfusion imaging by PET is that existing perfusion radiotracers such as $^{15}$O-water, $^{13}$N-ammonia or $^{82}$Rb-chloride have short half-lives. The use of these existing perfusion radiotracers requires an onsite or nearby cyclotron (for $^{15}$O-water and $^{13}$N-ammonia) or costly periodic replacement of the generator (>$30,000 per 4-6 weeks for $^{82}$Rb-chloride) for tracer production and limits their clinical availability.

$^{18}$F labeled radiotracers may be used for perfusion imaging. However, the combination of two $^{18}$F labeled radiotracers for flow-metabolism imaging in the same subject may necessitate a prolonged separation between the flow and metabolism scans because of the long half-life (110 minutes) of the $^{18}$F isotope, resulting in longer testing time and higher radiation exposure. Hybrid modalities like dynamic contrast-enhanced CT or MRI could also be used for perfusion imaging in combination with FDG-PET. However, each of these methods have drawbacks such as increased radiation dose by perfusion CT, potential renal toxicity induced by MRI contrast media, and the limited field-of-view for dynamic 3D CT or MRI data acquisition.

According to various embodiments, dynamic $^{18}$F-fluorodeoxyglucose ("$^{18}$F-FDG" or "FDG") PET imaging may be used to derive blood flow from the early phase (e.g., first 2 minutes) of FDG uptake without the need for a second flow-specific radiotracer. FDG is commonly used to assess glucose metabolism using PET imaging approximately forty-five minutes after administration. By use of tracer kinetic modeling, it is possible to also quantify blood flow using FDG. FDG blood-to-tissue delivery rate $K_1$ can be used as a surrogate of tumor blood flow. FDG $K_1$ not only reflects blood flow but also is related to the expression of glucose transporter. Thus, the dynamic FDG-PET method offers a potential for integrated flow-metabolism imaging using a single FDG injection. The effectiveness of using $K_1$ for representing blood flow via FDG is strongly dependent on the extraction fraction of FDG in tissue, which can vary from subject to subject and tissue region to tissue region. Using $K_1$ to approximate blood flow can be accurate for regions of high FDG extraction fraction (e.g., aggressive tumors), but is so far ineffective in regions of low FDG extraction fraction, such as in most organ tissue regions (e.g., brain, myocardium, renal cortex) and low-grade tumors.

Systems and methods are disclosed for a new high temporal-resolution (HTR) imaging methodology that leverages early-dynamic $^{18}$F-FDG PET for quantitative blood flow imaging. Early-dynamic PET is characterized by being conducted relatively early after tracer administration and at relatively high temporal resolution. Temporal resolution may refer to time intervals at which a plurality of images are acquired. The HTR method increases the temporal sampling of dynamic PET from current 5-10 seconds per time frame to less than about 2 seconds per frame. HTR imaging may better capture the first-pass perfusion process of a non-flow-specific radiotracer (e.g. $^{18}$F-FDG) than at the standard temporal resolution. HTR imaging may be used to quantify the perfusion parameters more accurately than standard temporal-resolution imaging, in particular for regions of relatively low FDG extraction fraction (e.g., less than about 0.5). Further, instead of using $K_1$ to estimate blood flow, $K_1$ and blood flow can be separately determined using a time-varying kinetic model. Accordingly, in contrast to prior methods, the early phase after administration of a tracer suitable for quantifying a parameter such as glucose metabolism can be leveraged to quantify blood flow, regardless of extraction fraction. This allows for multiparametric imaging with reduced imaging time, cost, and radiation exposure, as compared to previous two-tracer methods. Further, using PET to quantify more than one parameter obviates the need to do different types of scans, eliminating problems such as increased radiation dose by CT, potential renal toxicity from MRI contrast media, and the limited field-of-view for dynamic 3D CT or MRI data acquisition.

The method may be described with respect to FDG, as one example. However, the HTR imaging method of this disclosure is widely applicable to other intravenously injected radiotracers. Examples include, but are not limited to, $^{18}$F-fluciclovine for prostate cancer, $^{18}$F-AV-45 and similar tracers for Alzheimer's disease (AD), and $^{68}$Ga-DOTATATE for neuroendocrine tumors.

FIGS. 1A-1C show a comparison of standard temporal resolution and HTR sampling for early-dynamic FDG-PET. FIG. 1A illustrates an activity vs. scan time plot 102 for standard temporal resolution 102B (10-s, dotted line) and high temporal resolution 102A (2-s, solid line) sampling for early-dynamic FDG-PET in the descending aorta. FIG. 1B illustrates an activity vs. scan time plot 104 for standard temporal resolution 104B (10-s, dotted line) and high temporal resolution 104A (2-s, solid line) sampling for early-dynamic FDG-PET in a renal region of interest. HTR better captures the peaks of the blood and renal time activity curves (TAC). While the renal TAC in FIG. 1B contains noise, the peak signal can be verified on the low-noise TAC extracted from the whole right kidney 106, as shown in FIG. 1C (HTR, solid line 106A; standard temporal resolution, dotted line 106B).

New PET kinetic modeling and image reconstruction methods are disclosed to overcome the challenges encountered in HTR dynamic PET imaging. The teachings of this disclosure establish a new HTR methodology to enable quantitative FDG-perfusion imaging for dual-functional evaluation of flow-metabolism using a single dose of $^{18}$F-FDG for PET scanning.

Embodiments provide a method for quantitative blood flow imaging using the classic metabolic radiotracer $^{18}$F-FDG. Such a method can be applied to image flow-metabolism mismatch or coupling that has broad clinical and scientific significance. This new dimension of perfusion may be applied to many other PET radiotracers (e.g., amyloid, tau, inflammation, hypoxia, and dopamine tracers). Embodiments enable a new single-tracer multiparametric imaging methodology to study the coupling or mismatch between perfusion and key molecular processes in many of the major diseases, including cancer, heart diseases and Alzheimer's disease.

C. HTR Early-Dynamic PET

A tracer (e.g., FDG, $^{18}$F-fluciclovine, $^{18}$F-AV-45, etc.) may be introduced into the body of a subject. A set of PET images may be acquired, of at least a portion of the body, substantially immediately after tracer administration. For early PET, the set of PET images may be obtained within about two minutes of tracer administration. In contrast, in conventional systems for imaging of a radiotracer for example, it is common to wait one hour before executing a PET scan, to account for the time taken to metabolize the radiotracer.

Conventional clinical FDG-based PET imaging is commonly executed using a long exposure, static image. Alternatively, low-temporal resolution scans have been done in a laboratory setting using a standard temporal resolution of approximately 5-10 seconds per frame.

In HTR scanning, images are acquired at a plurality of predetermined time intervals of about two seconds or less. Images may be acquired in intervals of about 1.5-2.5 seconds, about 1-2 seconds, about 0.5-1 second, or about 0.5 seconds or less. Images may be acquired in a plurality of intervals for a period of about one to ten minutes. Alternatively, longer dynamic scans may be conducted (e.g., 10-30 minutes or 30-60 minutes) to acquire additional data.

For tracer-tissue combinations with a relatively low extraction fraction (e.g., below about 0.5), using a standard temporal resolution of 5-10 seconds, it is possible to miss the tracer being transported into tissue due to the fast tracer kinetics. By using a higher temporal resolution (e.g., 2 seconds or less), the transport of the tracer into tissue may be captured. Further, the increased temporal resolution can be used to quantify better estimates of the kinetic parameters, as compared to standard compartmental modeling.

As a technical challenge with HTR imaging in PET, standard tracer kinetic modeling is inadequate for analyzing HTR data. Compartmental modeling has been used in dynamic PET. Standard compartmental modeling assumes that radiotracer is instantaneously mixed and uniformly distributed in each compartment. This assumption can work well for dynamic PET of standard temporal-resolution (5-10 s). When temporal resolution is high, the assumptions of standard compartmental modeling fail, and estimates of kinetic parameters diverge from the actual values. This problem can be solved using the new time-varying kinetic model, described below in Section D.

Advantageously, a tracer specialized for measuring another parameter, other than blood flow, may be used with the HTR imaging method. The tracer may first be used to quantify blood flow with the HTR imaging method. Next, the tracer may be used to quantify another parameter. For example, $^{18}$F-fluorodeoxyglucose may be used to measure blood flow and to quantify glucose metabolism. As another example, $^{18}$F-fluciclovine may be used to quantify blood flow and quantify an uptake of amino acid transporters. As another example, $^{18}$F-AV-45 may be used to quantify blood flow and to quantify an amyloid load. As another example, $^{68}$Ga-DOTATATE may be used to quantify blood flow and to quantify an expression of somatostatin receptors. The additional parameter(s) may be obtained by obtaining additional PET scans (e.g., by acquiring a single image and/or a second set of images) or by a continuous long dynamic scan substantially immediately after tracer injection.

D. HTR Time-Varying Kinetic Modeling

Standard compartmental modeling in dynamic PET assumes time-constant tracer kinetics and does not accurately model HTR early-dynamic PET data. A new modeling approach and algorithm is disclosed herein, based on ordinary differential equations with time-varying parameters. While the prior method of estimating blood flow as $K_1$ by standard compartmental modeling only works for regions of high FDG extraction fraction (e.g., >0.5), the new time-varying kinetic modeling strategy can also work for regions of low FDG extraction fraction (e.g., <0.5).

FIG. 2 illustrates a standard 3-compartment model for FDG kinetics 200. FDG is transported from plasma to tissue cells with the delivery rate $K_1$ (the "blood-to-tissue delivery rate") and from tissue to plasma with the rate $k_2$ (the "tissue-to-blood delivery rate"). FDG is phosphorylated in cells into FDG 6-phosphate with the rate $k_3$ and the phosphorylation process can be reversed at the rate $k_4$. The total activity measured by PET is:

$$C_T(t)=(1-f_v)[C_1(t)+C_2(t)]+f_v C_{wb}(t),$$

with $f_v$ denoting the fractional blood volume. $C_{wb}(t)$ is the FDG activity in the whole-blood and can be approximated by $C_p(t)$.

Although $K_1$ is often used as a surrogate for blood flow, the $K_1$ parameter is generally not the same as blood flow F. This is shown by the classic Renkin-Crone model, $$K_1 = F \cdot E = F \cdot [1-\exp(-PS/F)],$$

where E denotes radiotracer extraction fraction. The extraction fraction E may be determined as a function of the blood flow F and the product of tracer permeability (P) and surface area (S) in a tissue region. If E is large (PS>>F), then $K_1 \approx F$. If E is small (PS<<F), then $K_1 \approx PS$. This suggests that $K_1$ approximates blood flow for regions of high FDG extraction fraction (e.g., aggressive tumors). However, the extraction fraction of FDG is commonly low in many tissue regions and FDG $K_1$ does not represent blood flow closely.

Figure 3A:
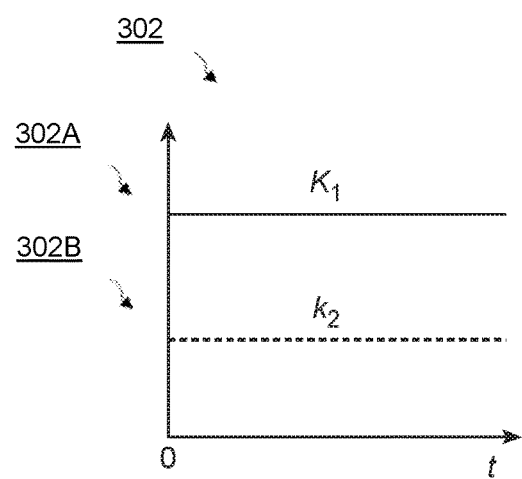
FIG. 3A illustrates a standard compartmental model with constant $K_1$ and $k_2$.

FIG. 3A illustrates a standard compartmental model 302 with constant $K_1$ 302A and $k_2$ 302B. Compartmental modeling is widely used for analyzing time activity curves (TACs) in dynamic PET. The FDG delivery rate $K_1$ has been used as a surrogate of blood flow. The parameters $k_3$ and $k_4$ are neglected if only the very-first few minutes (e.g., first 2 minutes) are used in early-dynamic PET. However, standard compartmental modeling may not fit the HTR early-dynamic FDG-PET data well. This incapability of standard modeling can be explained by the inherent limitations of the underlying assumptions of compartmental modeling: that radiotracer is instantaneously mixed and uniformly distributed in compartments. The assumption may be violated when temporal resolution increases and HTR imaging captures additional information of heterogeneous behaviors of radiotracer transport. The standard 2-compartment model (as shown in FIG. 3A, with $k_3$ and $k_4$ neglected) corresponds to $K_1$ and $k_2$ being constants over time.

Tracer arrival delay and physiological dispersion of blood input have been commonly ignored in dynamic FDG-PET studies. These two factors may not affect kinetic parameter estimation significantly in standard compartmental modeling given the limited temporal resolution of 5-10 s. However, their effects on accurate kinetic parameter estimation become more and more important as the temporal resolution of early-dynamic PET is improved to 1-2 seconds and the focus is on estimation of blood flow.

Figure 3B:
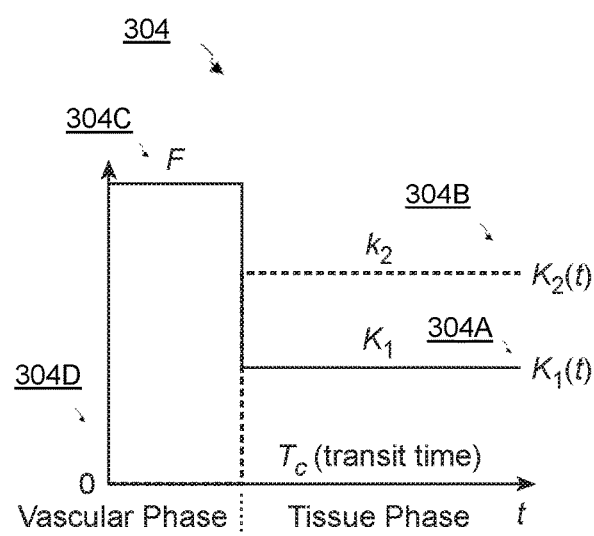
FIG. 3B illustrates a time-varying kinetic model for early-dynamic PET according to various embodiments.

FIG. 3B illustrates a time-varying kinetic model 304 for early-dynamic PET. The time-varying model divides the tracer uptake period into a vascular phase and a tissue phase, allowing the estimation of blood flow F 304C in addition to $K_1$. In comparison to the standard model of FIG. 3A, the new time-varying 2-compartment model (FIG. 3B) defines a transit time $T_c$ to divide the tracer uptake period into a vascular phase 304D and a tissue phase 304E. In the vascular phase ($t \leq T_c$), $K_1(t)$ 304A represents blood flow F and $k_2(t)$ 304B is 0. In the tissue phase ($t > T_c$), $K_1(t)$ 304A represents $K_1 = FE$ and $k_2(t) = k_2$ (304B) with the same meanings as in standard compartmental modeling. In this way, blood flow F is estimated separately from $K_1$. The time-varying model has five time-varying kinetic parameters ($f_v$, F, $k_2$, E, $T_c$) as compared to three kinetic parameters ($f_v$, $K_1$, $k_2$) in the standard model. The time-varying model is further characterized by the kinetic parameters ($K_1(t)$, $k_2(t)$, etc.) varying with time.

1. The Model

The time-varying kinetic model includes time-varying parameters $K_1(t)$ (tracer delivery rate from blood into tissue as a function of time) and $k_2(t)$ (tracer delivery rate from tissue to blood as a function of time). The time-varying kinetic model may further include time-varying parameters $k_3(t)$ (a rate at which the tracer is phosphorylated in cells as a function of time) and/or $k_4(t)$ (the rate at which phosphorylation of the tracer in the cells is reversed as a function of time). The time-varying kinetic model may further jointly consider tracer arrival delay and dispersion.

The blood input function $C_p(t)$ may be described using cubic b-splines $$C_p(t) = \Sigma_{m=1}^{M} v_m b(t-t_m),$$

where $b(t-t_m)$ denotes the cubic b-spline located at each middle frame time $t_m$ and $v_m$ is the corresponding coefficient. $v_m$ can be obtained by b-spline filtering. The actual blood input for an organ may be modeled as a function of the tracer arrival delay $t_d$ and dispersion parameter $k_\tau$:

$$C_{in}(t; t_d, k_\tau) = C_p(t-t_d) \otimes [k_\tau \exp(-k_\tau t)]$$

The model parameters $t_d$ and $k_\tau$ may be jointly estimated with other kinetic parameters ($f_v$, F, $k_2$, E, $T_c$) through weighted least squares minimization of tissue TAC fitting. This may be implemented, for example, using a basis function algorithm.

2. Extended Time-Varying Kinetic Modeling Method for Longer Scans.

The time-varying 2-compartment model (as shown in FIG. 3B) is tailored to very-early dynamic scan (e.g., first 2 minutes after administration of a radiotracer). Use of a longer scan (e.g., 10 minutes) may be helpful to control noise and obtain more robust estimation of blood flow F. However, as the scan time gets longer, the assumption that $k_3 = 0$ may no longer hold true. To identify the best model and scan time, a more general time-varying modeling framework may be used by extending the time-varying model from 2-compartment to 3-compartment. This extension may allow the investigation of longer scan time for time-varying kinetic modeling.

The generalized framework is described by the following time-varying ordinary differential equations, $$\frac{d}{dt}\begin{bmatrix} C_1(t) \\ C_2(t) \end{bmatrix} = \begin{bmatrix} -[K_2(t)+K_3(t)] & K_4(t) \\ K_3(t) & -K_4(t) \end{bmatrix}\begin{bmatrix} C_1(t) \\ C_2(t) \end{bmatrix} + \begin{bmatrix} K_1(t) \\ 0 \end{bmatrix} C_p(t)$$

This model is very similar to standard time-constant 3-compartmental model but here the kinetic parameters are denoted as time-varying. The functions $k_3(t)$ and $k_4(t)$ have a similar time-varying shape as $k_2(t)$ illustrated in FIG. 3B. An analytical solution may be derived, for example, using linear time-varying system theory.

For TAC fitting using the time-varying model, weighted least squares optimization may be used. The brute-force basis function algorithm becomes inefficient as the number of unknown parameters increases. The Levenberg-Marquardt (LM) algorithm may be adopted for fast implementation. However, implementation of the LM algorithm is not straightforward for the time-varying model because the time-varying functions have break points at the time $T_c$. Further, as can be seen in FIG. 3B, the first-order derivatives of $K_1(t)$ and $k_2(t)$ are discontinuous.

Figure 4:
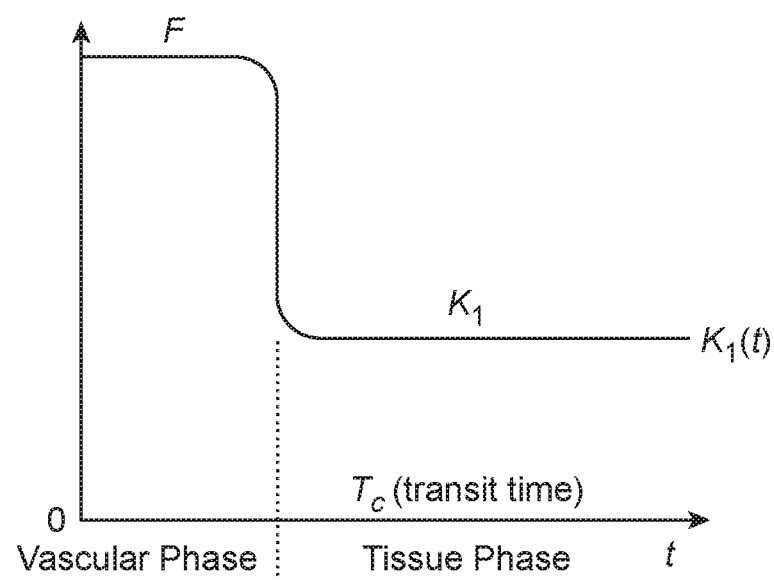
FIG. 4 illustrates a modified time-varying model using the smooth Heaviside function according to various embodiments.

The time-varying functions may be modified based on the model's mathematical connection with the Heaviside function H(t). For example, $$K_1(t) = F \cdot [1 - H(t-T_c)] + K_1 \cdot H(t-T_c)$$

is discontinuous at $t = T_c$. However, we can replace H(t) with its smooth version $$H_\epsilon(t) = \frac{1}{2}\left[1 + \frac{2}{\pi}\arctan\left(\frac{t}{\epsilon}\right)\right],$$

where $\epsilon$ is a small value (e.g., 0.1) to make the function smoothly continuous. The graphical illustration 400 for the resulting smooth $k_1(t)$ is shown in FIG. 4. Use of the smooth Heaviside function allows the implementation of the gradient-based LM algorithm for time-varying modeling.

Figure 5:
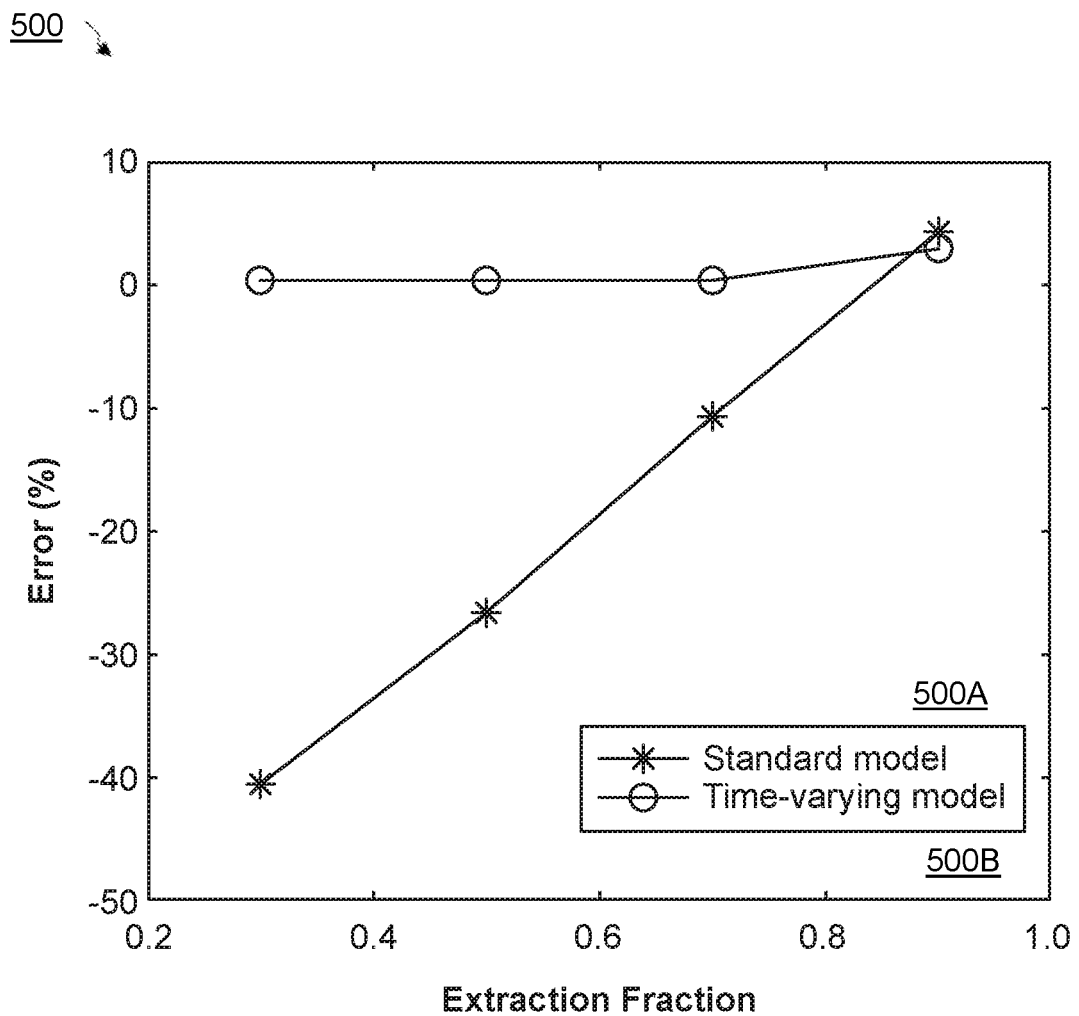
FIG. 5 illustrates error of a standard compartmental model ($K_1$) and the new time-varying model (F) for estimating blood flow from simulated HTR data of different extraction fractions according to various embodiments.

FIG. 5 shows the results 500 of an exemplary computer simulation study on the error of estimating blood flow using the time-varying model and standard model. The 2-minute TACs were simulated using the AATH model with $f_v=0.1$, $F=1.5$ mL/g/min, $k_2=0.8$ min$^{-1}$, $T_c=10$ s and different FDG extraction fractions $E=0.3$, 0.5, 0.7 and 0.9. The time-varying model 500B has demonstrated a stable identifiability for F across different E values. The $K_1$ method by standard compartmental modeling 500A induces an increasing error as E decreases, though it provides a good estimate of blood flow when the extraction fraction E is large.

FIGS. 6A-8B show results of a patient study illustrating the feasibility of the new model for analyzing HTR early-dynamic FDG data. The study includes 28 subject scans with the kidneys in the field of view. The estimated renal kinetics by the new model are $f_v=0.07\pm0.05$, $F=1.62\pm0.43$ mL/g/min, $k_2=0.81\pm0.28$ min$^{-1}$, $E=0.38\pm0.08$, and $T_c=13.00\pm3.06$ s.

Figure 6A:
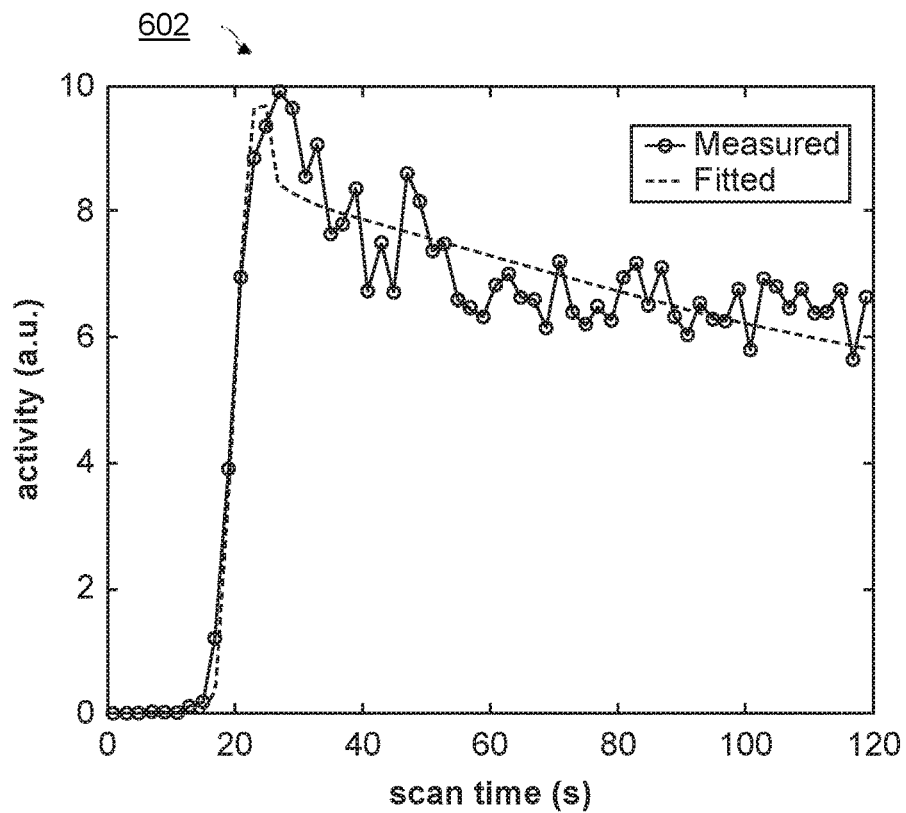
FIGS. 6A-6B illustrate a comparison of a time-varying model with a standard model for fitting subject data according to various embodiments.
Figure 6B:
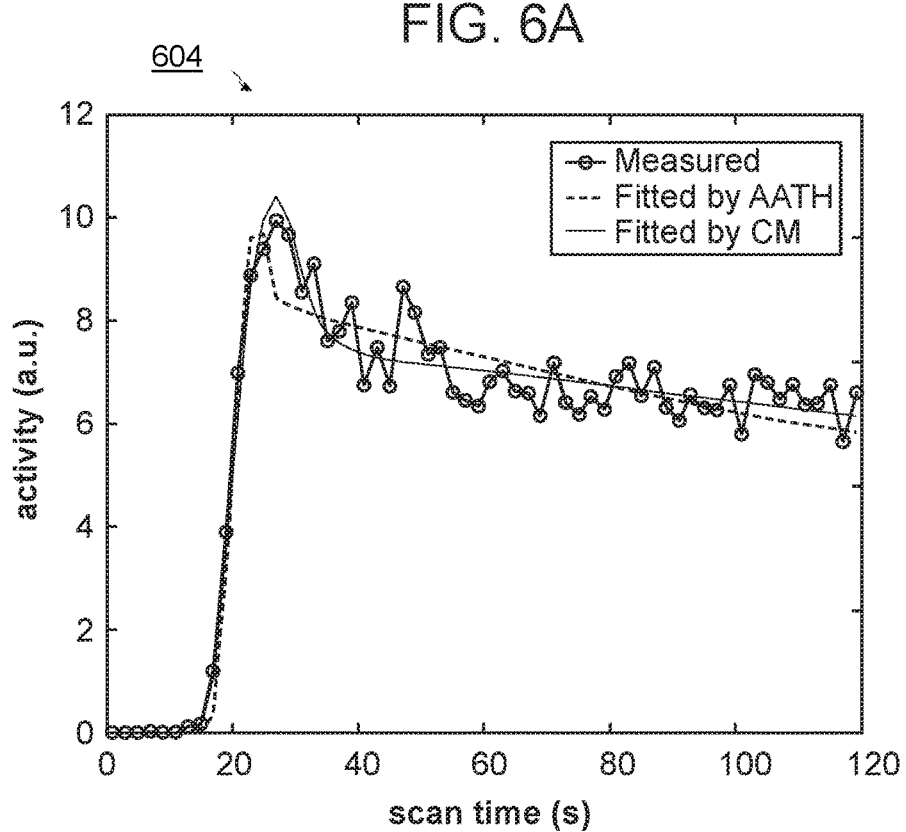

FIGS. 6A-6B illustrate a comparison of a time-varying model with a standard model for fitting subject data corresponding to an example TAC from the renal cortex. FIG. 6A illustrates activity (e.g., intensity of the applied radiotracer) as a function of time using the standard model for renal TAC 602. FIG. 6B illustrates the activity as a function of time using the new time-varying model for the renal TAC 604. The new model 604 can better fit the renal TAC than the standard model 602, which is particularly clear near the peak at around 25 s. The peak of the TAC was better fitted by the new model with a lower Akaike information criteria (AIC) value. The AIC value provides an estimate of the relative quality of statistical models to a data set. The lower the AIC value, the better the fit.

Figure 7A:
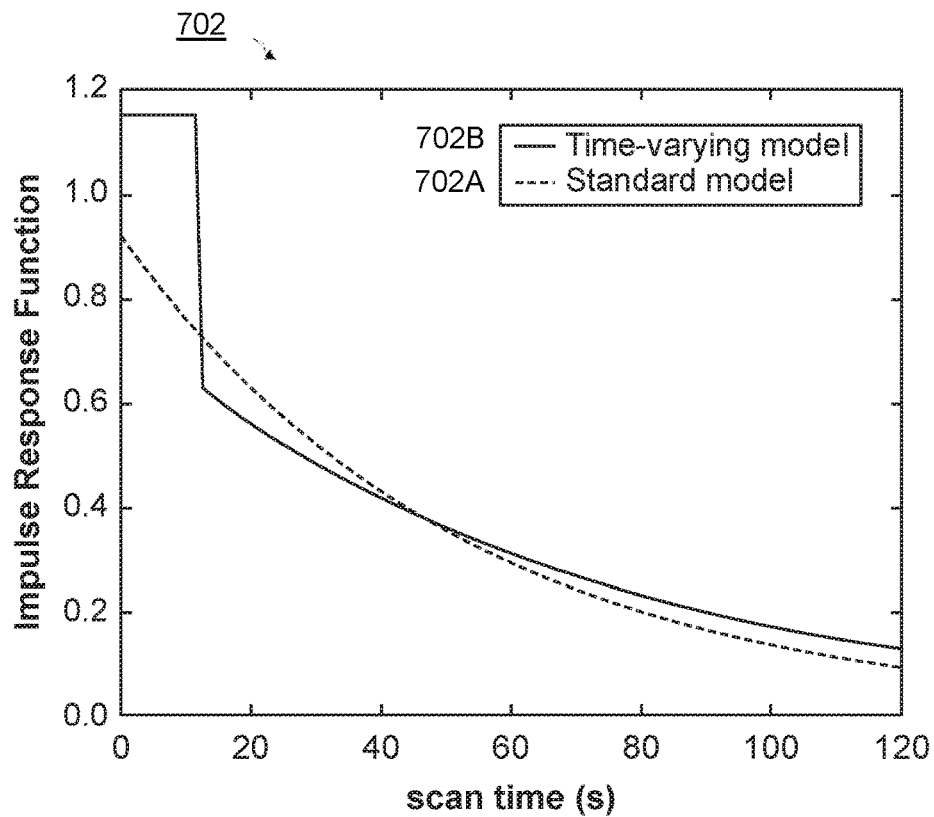
FIGS. 7A-7B illustrate a comparison of a time-varying model with a standard model for fitting subject data according to various embodiments.
Figure 7B:
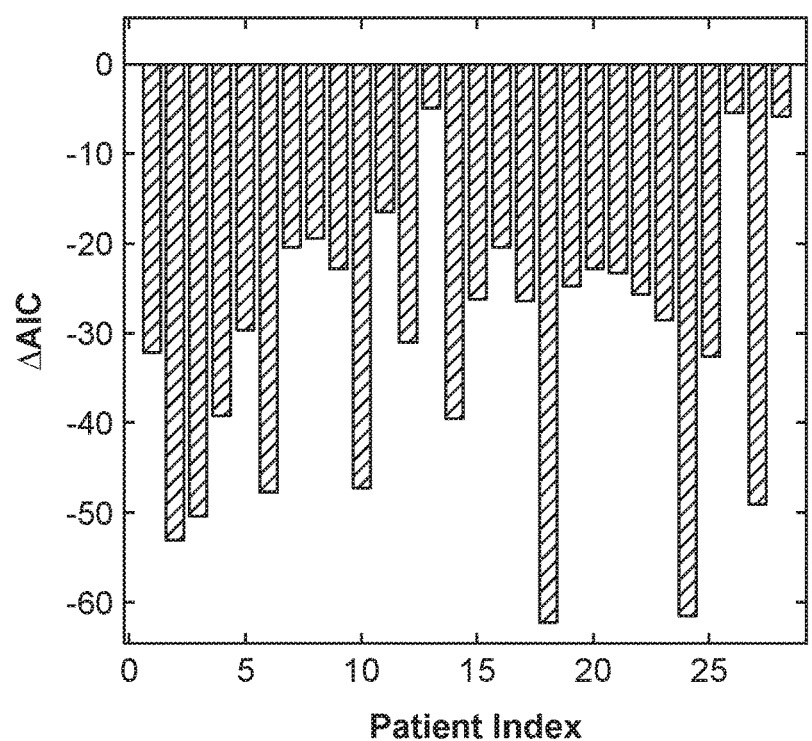

FIGS. 7A-7B illustrate a comparison of a time-varying model with a standard model for fitting subject data. FIG. 7A shows impulse response functions 702. As shown in FIG. 7A, the standard model 702A (dotted line) and time-varying model 702B (solid line) lead to different impulse functions. As shown in FIG. 7B, the better fit is confirmed by calculation of the AIC difference 704 between the two fits for 28 subjects. The negative differences in AIC between the two models indicate the new model is more appropriate for fitting the HTR TACs.

Figure 8A:
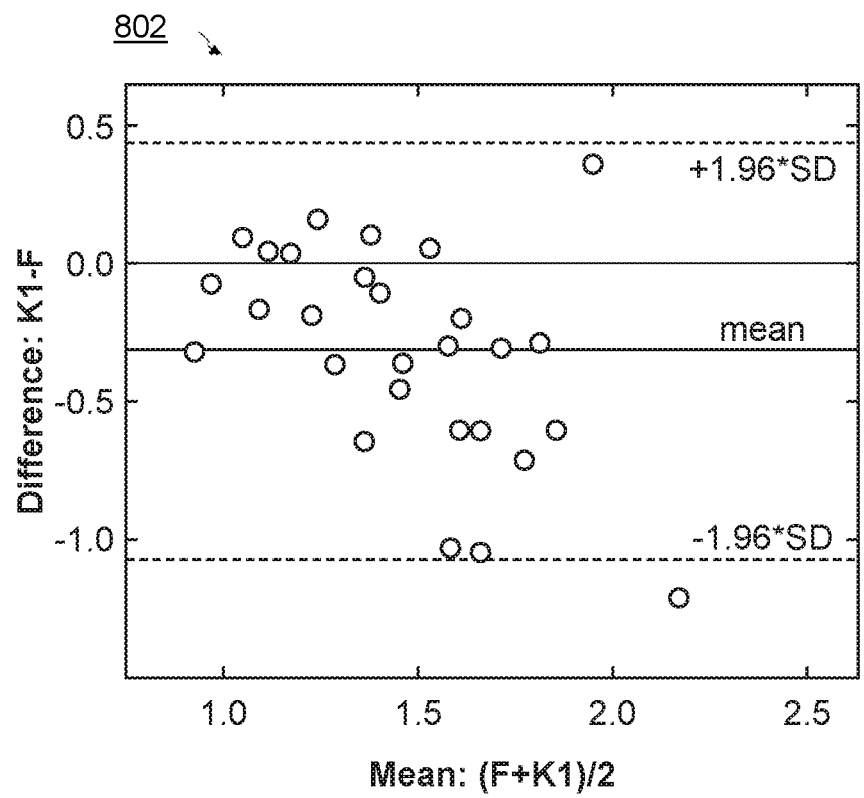
FIGS. 8A-8B illustrate that $K_1$ and F are not interchangeable at low extraction fraction according to various embodiments.
Figure 8B:
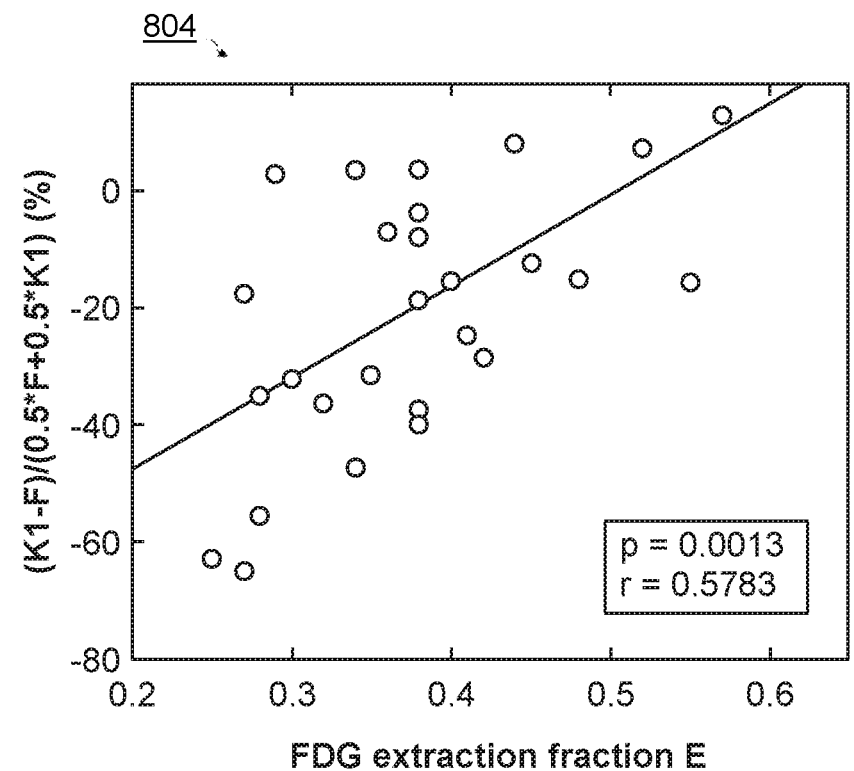

FIGS. 8A-8B illustrate that $K_1$ and F are not interchangeable at low extraction fraction. FIG. 8A shows a Bland-Altman plot 802 of F of the new model and $K_1$ of the standard model. The difference characterized by ±1.96 times the standard deviation (SD) is large (~1.5 mL/g/min), suggesting the two methods are not interchangeable according to absolute quantification. As shown in FIG. 8A, the Bland-Altman plot 802 indicates that F, derived by the time-varying model and $K_1$, derived by the standard model, are not interchangeable, given the large difference as determined by ±1.96SD. FIG. 8B shows the difference between F and $K_1$ tended to increase as the estimated FDG extraction fraction becomes smaller (804). As shown in FIG. 7B, the difference between $K_1$ and F has the trend of increasing as FDG extraction fraction decreases. The trend is consistent with the results from simulation.

E. Example Embodiment

The following example is described for purposes of clarity. Components and/or operations described in the example are specific examples which may not be applicable to certain embodiments, and should not be construed as limiting the scope of any of the claims.

According to an exemplary embodiment, a subject has a brain tumor to be analyzed. In particular, altered blood flow and glucose metabolism are closely related to two hallmarks of cancer. Thus, both blood flow and glucose metabolism are to be determined. To avoid the need to administer two tracers, a time-varying model is applied to HTR PET data for multiparametric imaging.

A single tracer, 18F-fluorodeoxyglucose (18F-FDG), is administered to the body of the subject by injection. Substantially immediately after administering the single tracer, a first set of images is acquired, via PET, of the portion of the body of the subject containing the brain tumor.

The first set of images is acquired for quantifying blood flow in a region of interest in the portion of the body of the subject containing the brain tumor. The first set of images is acquired in one-second intervals over the course of ten minutes (e.g., at a plurality of time intervals, each of the time intervals being equal to one second).

Based on the first set of images, an intensity of the tracer in the region of interest is determined as a function of time. For each image, of the set of images, the region of interest containing the tumor is selected. The activity, or intensity of the tracer, in the selected region of interest is determined. The activity is determined based on a pixel-by-pixel count of intensity in the image across the region of interest. The change in this intensity from one image to the next in the set of images represents the intensity of the tracer as a function of time. This tracer intensity over time may be plotted, similar to the activity vs. scan time plots shown in FIGS. 1A-1C.

The intensity of the tracer in the region of interest as a function of time is modeled using the time-varying kinetic model $$\frac{d}{dt}\begin{bmatrix} C_1(t) \\ C_2(t) \end{bmatrix} = \begin{bmatrix} -[K_2(t)+K_3(t)] & K_4(t) \\ K_3(t) & -K_4(t) \end{bmatrix}\begin{bmatrix} C_1(t) \\ C_2(t) \end{bmatrix} + \begin{bmatrix} K_1(t) \\ 0 \end{bmatrix}C_p(t),$$

wherein $$K_1(t)=F\cdot[1-H_\in(t-T_c)]+K_1\cdot H_\in(t-T_c)$$

is solved to determine the kinetic parameters $K_1(t)$, $K_2(t)$, $K_3(t)$, and $K_4(t)$, and $F(t)$, as described above in Section D. The determined parameter $F(t)$ corresponds to the blood flow through the region of interest.

After determining the blood flow, glucose metabolism in the region of interest can be determined. After a second time interval of approximately 20 minutes, a second set of images of the region of the body comprising the brain tumor is acquired using PET. The second set of images is then used to estimate glucose metabolism.

F. Applications

The HTR early-dynamic FDG-PET method of blood flow imaging has many clinical applications. As an example, myocardial flow may be imaged in the context of myocardial viability in ischemic cardiomyopathy. As another example, the above method may be used for tumor perfusion imaging for head-and-neck cancer.

FDG-PET has already been used and plays a critical role in patient management when assessing myocardial viability and head-and-neck cancer. Specifically, flow-metabolism mismatch has been used in the clinic for myocardial viability assessment in patients with ischemic cardiomyopathy. Integrated evaluation of tumor blood flow and glucose metabolism has also found to be useful for characterization of head-and-neck cancer.

An HTR early-dynamic scan for perfusion imaging may be added to existing FDG-PET protocols. Without the HTR method and time-varying kinetic model, a different tracer would be required to estimate blood flow. Here, on the other hand, tracers traditionally used for estimating other parameters such as glucose metabolism can be used to leverage the previously unused early period after tracer administration to quantify blood flow. This reduces the amount of tracers to which the subject is exposed, as well as the imaging time. Thus, the success of the HTR method combining blood flow and metabolism quantification in a dual-parametric flow-metabolism evaluation will have a high clinical impact. Reference methods for perfusion imaging are available in these diseases to evaluate the success of the proposed HTR method. Clinical myocardial viability tests already include a $^{13}$N-ammonia or $^{82}$Rb-chloride PET scan for myocardial perfusion imaging. Dynamic contrast-enhanced MRI has been used for perfusion imaging of brain tumor and head-and-neck tumor. Thus, the effectiveness of the HTR method for perfusion imaging can be validated using these reference methods.

FDG extraction fraction in the myocardium is relatively low, allowing an appropriate demonstration of the improvement of the new HTR method over the conventional FDG $K_1$ method. While aggressive cancer is associated with high FDG extraction, a large head-and-neck tumor can be spatially inhomogeneous and may consist of both acute hypoxia region (aggressive) and chronic hypoxia region (less aggressive), therefore suitable for quantifying the improvement of the HTR method.

Figure 9A:
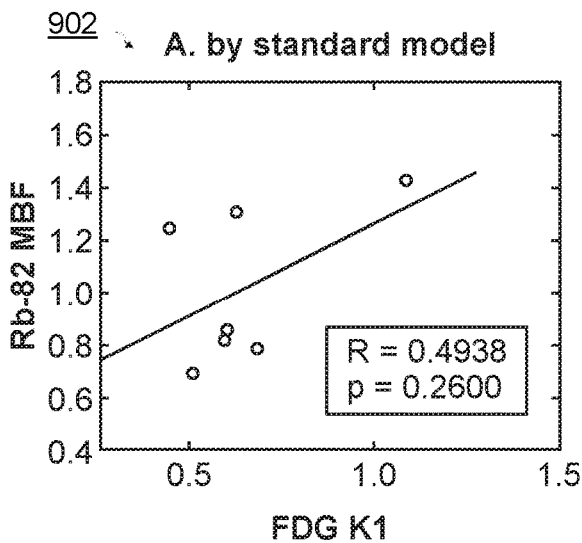
FIGS. 9A-9C show preliminary results of high temporal-resolution early-dynamic FDG-PET for myocardial blood flow quantification using Rb-82 PET as the reference according to various embodiments.
Figure 9B:
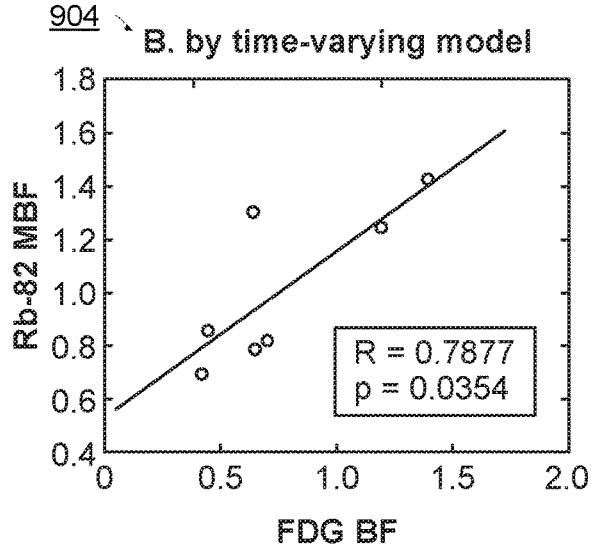
Figure 9C:
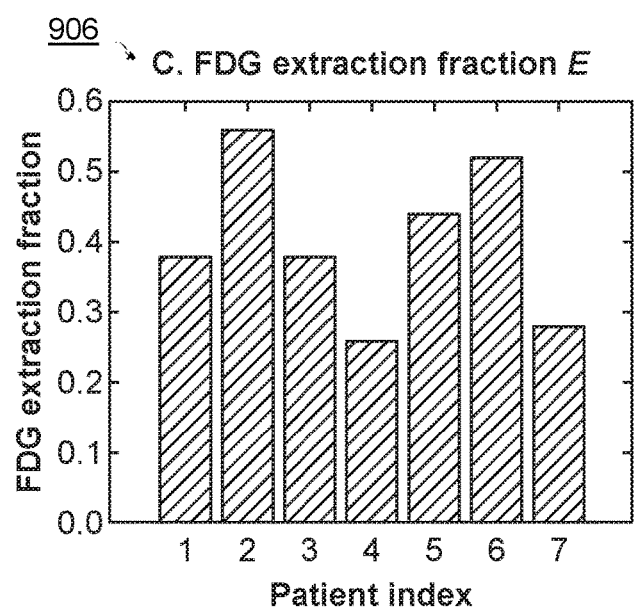

FIGS. 9A-9C show preliminary results of high temporal-resolution early-dynamic FDG-PET for myocardial blood flow quantification using Rb-82 PET as the reference. A study was conducted using $^{82}$Rb-PET/FDG-PET subject datasets to test whether $K_1$ and other kinetic parameters ($k_2$, $k_3$, $K_i$) by standard dynamic FDG-PET can be used to predict myocardial blood flow (MBF). The results are shown for seven subjects.

FIG. 9A shows results from the seven subjects for correlating MBF by Rb-82 PET with FDG $K_1$ by standard compartment modeling of HTR early-dynamic FDG scans (902). FIG. 9B shows results from the subjects with FDG blood flow F by time-varying kinetic modeling (904). FDG $K_1$ tended to correlate with Rb-82 MBF (r=0.4938, p=0.2600) but did not achieve statistical significance (p>0.05). In comparison, the FDG flow F by time-varying modeling had a higher correlation (r=0.7877) with Rb-82 MBF and demonstrated statistical significance (p=0.0354). FDG $K_1$ did not correlate with FDG F (r=0.5404, p=0.2104). The improvement of FDG F over FDG $K_1$ can be explained by the ability of time-varying modeling to account for the effect of low myocardial FDG extraction fraction (e.g., E<0.3) that presented in some subjects. FIG. 9C shows the FDG extraction fraction E for each of the seven subjects (906).

The reference MBF did not correlate with either FDG $K_1$ of standard modeling (r=0.3394, p=0.4564) or FDG F of the new model (r=0.4271, p=0.3392) when a standard temporal resolution of 10 s per frame is used for early-dynamic FDG-PET. This result indicates the importance of HTR for time-varying modeling.

A potential pitfall of the head-and-neck cancer application is that the size of carotid artery may not be large enough to provide accurate image-derived input function due to the partial volume effect. If it does not work (in terms of correlation with reference blood flow), a factor analysis algorithm may be applied to improve the extraction of image-derived input function. Alternatively, head-and-neck cancer patients may be scanned on a highly sensitive scanner (e.g., the EXPLORER scanner designed by the EXPLORER consortium, which has a 2-m long axial field of view) to allow the use of the left ventricle region to extract image-derived input function for the head-and-neck cancer study.

G. Advantages

The teachings of this disclosure have a number of advantages. First, radiotracers, such as the classic metabolic radiotracer $^{18}$F-FDG, may be used for quantitative perfusion imaging. The HTR development described herein can enable quantitative FDG-perfusion imaging, which not only works for regions of high FDG extraction fraction, but also is more broadly applicable to tissue regions of low to medium FDG extraction. Considering the wide availability of FDG, the new method will allow perfusion imaging widely accessible in clinics and research especially when flow-specific radiotracers are not available. This allows for flow-metabolism imaging with reduced imaging time, cost, and radiation exposure, and improved clinical accessibility. This will allow a single FDG injection to image both perfusion and metabolism (e.g., by an early-dynamic scan plus a late scan or by a full dynamic scan), thus eliminating the need for a flow-specific radiotracer. In contrast to conventional two-tracer flow-metabolism imaging, which is resource-intensive with long imaging time and significant cost, this HTR imaging method can make the evaluation of flow-metabolism mismatch much more easily and widely available to clinical cardiology (e.g. for myocardial viability assessment) and personalized cancer care (e.g., for evaluation of tumor aggressiveness).

Embodiments have a number of additional advantages. For example, the HTR imaging method may be used with other intravenously injected radiotracers (e.g., $^{18}$F-fluciclovine, $^{18}$F-AV-45, $^{68}$Ga-DOTATATE, etc.). The HTR early-dynamic method may add a new dimension of perfusion information to each of these FDA-approved radiotracers to create single-tracer multiparametric imaging for different clinical applications.

Additionally, the kinetic modeling methods described herein are also broadly applicable to many other PET imaging applications where dynamic imaging and higher temporal resolution are needed. Examples include dual-tracer or multi-tracer PET imaging and PET imaging of transient neurotransmitter release.

H. Computer Components; Extensions

It should be understood that any of the embodiments be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present disclosure using hardware and a combination of hardware and software.

Any of the software components or functions described in this application may be implemented as software code to be executed by a processor using any suitable computer language such as, for example, Java, C, C++, C #, Objective-C, Swift, or scripting language such as Perl or Python using, for example, conventional or object-oriented techniques. The software code may be stored as a series of instructions or commands on a computer-readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer-readable medium may be any combination of such storage or transmission devices.

Such programs may also be encoded and transmitted using carrier signals adapted for transmission via wired, optical, and/or wireless networks conforming to a variety of protocols, including the Internet. As such, a computer-readable medium according to an embodiment may be created using a data signal encoded with such programs. Computer-readable media encoded with the program code may be packaged with a compatible device or provided separately from other devices (e.g., via Internet download). Any such computer-readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

The above description is illustrative and is not restrictive. Many variations of the embodiments will become apparent to those skilled in the art upon review of the disclosure. The scope of the embodiments should, therefore, be determined not with reference to the above description, but instead should be determined with reference to the pending claims along with their full scope or equivalents.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

One or more features from any embodiment may be combined with one or more features of any other embodiment without departing from the teachings of this disclosure.

As used herein, the use of "a," "an," or "the" is intended to mean "at least one," unless specifically indicated to the contrary.

What is claimed is:

1. A method for quantifying blood flow through a portion of a body, the method comprising:
   introducing a single tracer into the body;
   acquiring, via positron emission tomography (PET), a first set of images of at least a portion of the body, wherein the first set of images is acquired at a first plurality of predetermined time intervals;
   based on the first set of images, determining an intensity of the tracer in the at least the portion of the body as a function of time;
   modeling the intensity of the tracer in the at least the portion of the body as a function of time using a time-varying kinetic model; and
   based on the time-varying kinetic model of the single tracer, quantifying (1) the blood flow through the at least the portion of the body and (2) one or more of a glucose metabolism, an uptake of amino acid transporters, an amyloid load, or an expression of somatostatin receptors in the at least the portion of the body.

2. The method of claim 1, wherein the predetermined time intervals are about 2 seconds or less.

3. The method of claim 1, further comprising identifying one or more of a blood-to-tissue delivery rate of the tracer as a function of time, a tissue-to-blood delivery rate of the tracer as a function of time, a rate at which the single tracer is phosphorylated in cells as a function of time, or a rate at which the phosphorylation of the single tracer in the cells is reversed as a function of time.

4. The method of claim 1, wherein the single tracer is one of: $^{18}$F-fluorodeoxyglucose, $^{18}$F-fluciclovine, $^{18}$F-AV-45, or $^{68}$Ga-DOTATATE.

5. The method of claim 1, wherein the at least the portion of the body comprises: a heart, a brain, a kidney, a lung, a liver, a spleen, a breast, a colon, a prostate, or a region containing a tumor.

6. The method of claim 1, wherein the at least the portion of the body comprises a region wherein an extraction fraction of the single tracer comprises less than about 0.5.

7. The method of claim 1, further comprising, after a second time interval, acquiring, via positron emission tomography (PET), a second set of images of the at least the portion of the body.

8. The method of claim 7, wherein the second set of images comprises a single image.

9. The method of claim 1, wherein a first image, of the first set of images, is acquired less than two minutes after the single tracer is administered.

10. The method of claim 1, wherein the time-varying kinetic model comprises a set of differential equations comprising time-varying parameters.

11. The method of claim 1, wherein the time-varying kinetic model comprises a smooth Heaviside function.

12. A system comprising:
    a processor; and
    a memory storing instructions that, when executed by the processor, cause the processor to:
    acquire, via positron emission tomography (PET), a first set of images of at least a portion of a body after a single tracer is introduced into the body, wherein the first set of images is acquired at a first plurality of predetermined time intervals;
    based on the first set of images, determine an intensity of the tracer in the at least the portion of the body as a function of time;
    model the intensity of the tracer in the at least the portion of the body as a function of time using a time-varying kinetic model; and
    based on the time-varying kinetic model of the single tracer, quantify (1) blood flow through the at least the portion of the body and (2) one or more of a glucose metabolism, an uptake of amino acid transporters, an amyloid load, or an expression of somatostatin receptors in the at least the portion of the body.

13. The system of claim 12, wherein the predetermined time intervals are about 2 seconds or less.

14. The system of claim 12, wherein the instructions, when executed by the processor, further cause the processor to:
    identify one or more of a blood-to-tissue delivery rate of the tracer as a function of time, a tissue-to-blood delivery rate of the tracer as a function of time, a rate at which the single tracer is phosphorylated in cells as a function of time, or a rate at which the phosphorylation of the single tracer in the cells is reversed as a function of time.

15. The system of claim 12, wherein the single tracer is one of: $^{18}$F-fluorodeoxyglucose, $^{18}$F-fluciclovine, $^{18}$F-AV-45, or $^{68}$Ga-DOTATATE.

16. The system of claim 12, wherein the at least the portion of the body comprises a region wherein an extraction fraction of the single tracer comprises less than about 0.5.

* * * * *